US012653474B2

(12) United States Patent
Maidment et al.

(10) Patent No.: US 12,653,474 B2
(45) Date of Patent: Jun. 16, 2026

(54) RADIOGRAPHIC CONTRAST AGENTS FOR TEMPORAL SUBTRACTION AND DUAL-ENERGY X-RAY IMAGING

(71) Applicant: The Trustees of the University of Pennsylvania, Philadelphia, PA (US)

(72) Inventors: Andrew D. A. Maidment, Villanova, PA (US); Anatoliy V. Popov, Philadelphia, PA (US); E. James Delikatny, Havertown, PA (US); Andrew Tsourkas, Bryn Mawr, PA (US); Roshan Karunamuni, Philadelphia, PA (US); Ajlan Al Zaki, Philadelphia, PA (US); Sara Gavenonis, Wilmington, DE (US); David Cormode, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 435 days.

(21) Appl. No.: 17/711,156

(22) Filed: Apr. 1, 2022

(65) Prior Publication Data

US 2022/0265234 A1    Aug. 25, 2022

Related U.S. Application Data

(62) Division of application No. 14/776,232, filed as application No. PCT/US2014/025769 on Mar. 13, 2014, now Pat. No. 11,337,665.

(60) Provisional application No. 61/788,891, filed on Mar. 15, 2013.

(51) Int. Cl.
| | |
|---|---|
| *A61B 6/00* | (2006.01) |
| *A61K 47/02* | (2006.01) |
| *A61K 47/10* | (2017.01) |
| *A61K 47/32* | (2006.01) |
| *A61K 49/04* | (2006.01) |

(52) U.S. Cl.
CPC .............. *A61B 6/481* (2013.01); *A61B 6/482* (2013.01); *A61K 47/02* (2013.01); *A61K 47/10* (2013.01); *A61K 47/32* (2013.01); *A61K 49/04* (2013.01); *A61K 49/0423* (2013.01)

(58) Field of Classification Search
None
See application file for complete search history.

(56) References Cited

U.S. PATENT DOCUMENTS

| | | | |
|---|---|---|---|
| 5,375,158 | A | 12/1994 | Logan |
| 2006/0115536 | A1 | 6/2006 | Yacaman et al. |
| 2011/0172523 | A1 | 7/2011 | Natan et al. |
| 2011/0208040 | A1 | 8/2011 | Carmi et al. |
| 2011/0300532 | A1 | 12/2011 | Jahnen-Dechent et al. |
| 2012/0238870 | A1 | 9/2012 | Smith et al. |

OTHER PUBLICATIONS

Boone, J., et al., "Molybdenum, rhodium and tungsten anode spectral models using interpolating polynomials with application to mammography," Oct. 1, 1997, pp. 1863-1874, vol. 24(12), Medical Physics (abstract only).

Brust, M. et al., "Synthesis of thiol-derivatized gold nanoparticles in a two-phase liquid-liquid system", 1994, pp. 801-802, Issue 7, Journal of the Chemical Society, Chemical Communications (abstract only).

Dance, D.R., "Monte-Carlo calculation of conversion factors for the estimation of mean glandular breast dose," 1990, pp. 1211-1219, vol. 35(9), Physics in Medicine and Biology (abstract only).

Garay et al. Antibodies against polyethylene glycol in healthy subjects and in patients treated with PEG-conjugated agents. 2012 Expert Opin. Drug Deliv. 9:1319-1323. (Year: 2012).

Graf, C., et al., "A General method to coat colloidal particles with silica", Jul. 11, 2003, pp. 6693-6700, vol. 19(17), Langmuir (abstract only).

Han et al. Reverse microemulsion-mediated synthesis of silica-coated gold and silver nanoparticles. 2008 Langmuir 24: 5842-5848. (Year: 2008).

Hendee W.R., et al., Medical Imaging Physics, 4th Edition, 2002, Wiley-Liss (NY).

Hussain, S.M., et al., "In vitro toxicity of nanoparticles in BRL 3A rat liver cells", Aug. 25, 2005, pp. 975-983, vol. 18, Toxicology in Vitro.

Kim et al. Antibiofouling polymer-coated gold nanoparticles as a contrast agent for in vivo X-ray computed tomography imaging. 2007 J. Am. Chem. Soc. 129: 7661-7665. (Year: 2007).

Kobayashi et al. X-ray imaging technique using colloid solution of Agl/silica/poly(ethylene glycol) nanoparticles. 2012 Materials Focus 1: 127-130. (Year: 2012).

Koole, R., et al., "Paramagnetic lipid-coated silica nanoparticles with a fluorescent quantum dot core; A New contact agent platform for multimodality imaging", Nov. 26, 2008, pp. 2471-2479, vol. 19 (12), Bioconjugate Chemistry (abstract only).

Liu et al., 2012 Colloids Surf. B Biointerfaces 94: 58-67, published online Jan. 25, 2012.

Navarro, E., et al., "Toxicity of silver nanoparticles to Chlamydomonas reinhardtii", Oct. 1, 2008, pp. 8959-8964, vol. 42(23), Environmental Science and Technology (abstract only).

NIST XCOM online physics database (National Institute of Standards and Technology (NIST) Physical Measurement Laboratory. XCOM: Photon Cross Sections Database. Date created: Sep. 17, 2009, Last Updated: May 19, 2015 (abstract only).

(Continued)

*Primary Examiner* — Michael G. Hartley
(74) *Attorney, Agent, or Firm* — BakerHostetler

(57) ABSTRACT

Contrast agents for x-ray imaging including stabilized metal nanoparticles and encapsulated nanoparticles, as well as methods for imaging tissue with these agents, are disclosed. Also disclosed are methods of dual energy x-ray imaging using metal nanoparticle contrast agents or encapsulated metal nanoparticles.

23 Claims, 13 Drawing Sheets

(56) References Cited

OTHER PUBLICATIONS

Pan et al. Computed tomography in color: NanoK-enhanced spectral CT molecular imaging. 2010 Angew. Chern. Int. Ed. Engl. 49:9635-9639. (Year: 2010).

Silvert, P.Y., et al., "Preparation of colloidal silver dispersions by the polyol process. Part 1—Synthesis and Characterization," 1996, pp. 573-577, vol. 6(4), Journal of Materials Chemistry (abstract only).

RADIOGRAPHIC CONTRAST AGENTS FOR TEMPORAL SUBTRACTION AND DUAL-ENERGY X-RAY IMAGING

CROSS-REFERENCE TO RELATED APPLICATION

This application is related to and claims the benefit of U.S. Provisional Application No. 61/788,891, entitled "A RADIOGRAPHIC CONTRAST AGENT FOR TEMPORAL SUBTRACTION AND DUAL-ENERGY BREAST X-RAY IMAGING BASED ON SILVER NANOPARTICLES" filed Mar. 15, 2013, the contents of which are incorporated herein by reference in their entirety and for all purposes.

GOVERNMENT INTEREST STATEMENT

This application is a divisional of now-allowed U.S. patent application Ser. No. 14/776,232 (filed Sep. 14, 2015); which is the U.S. National Phase application of PCT International Application No. PCT/US2014/025769 (filed Mar. 13, 2014); which claims priority to and the benefit of U.S. Provisional Application No. 61/788,891 (filed Mar. 15, 2013). The contents of the foregoing applications are incorporated herein by reference in their entirety and for all purposes.

FIELD OF INVENTION

Described herein are, silver nanoparticle contrast agents and encapsulated nanoparticles for x-ray imaging and methods for x-ray imaging of tissue using metal nanoparticle contrast agents and encapsulated nanoparticles.

BACKGROUND OF THE INVENTION

Contrast-enhanced dual-energy (DE) x-ray imaging provides a technique to increase the contrast of radiographic imaging agents by suppressing the variation in signal between various tissue types. In the breast, for example, this involves the suppression of the signal variation between admixtures of glandular and adipose tissue. By reducing the effect of this "anatomical noise", it is then possible to more accurately segment and quantify the signal from the contrast agent. Dual-energy imaging utilizes two distinct energy spectrums (low- and high-) to quantify the variation in attenuation with energy. To achieve a suitable contrast between imaging agent and tissue, it is therefore necessary that their respective attenuation profiles do not follow the same general trend from low- to high-energy. This can be done by using a contrast material whose It- edge lies between the two energy spectrums. The discrete jump in attenuation due to the photoelectric effect of the extra k-shell electrons means that the contrast material exhibits a markedly different attenuation profile to the surrounding tissue.

Currently, the majority of research that is performed in dual-energy x-ray imaging involves iodinated contrast agents. Silver (Ag) represents an attractive alternative due to the location of its k-edge (25.5 keV) within the range of clinically-used mammographic energies. Silver filtration is also used in the clinical setting, which could provide additional benefit with a silver imaging agent. There is a need to provide for silver in tissue, e.g., breast, DE x-ray imaging, and to develop silver and other metal nanoagents for use in living systems.

SUMMARY OF THE INVENTION

In one aspect, provided herein are contrast agents for x-ray imaging, the contrast agents comprising stabilized metal nanoparticles. Also provided herein are methods of x-ray imaging of tissue (e.g., breast tissue) in a subject (e.g. a human), comprising administering any of the stabilized metal nanoparticles described herein.

In another aspect, provided herein are composition of encapsulated nanoparticles, an encapsulated nanoparticle includes: (a) a metallic core; (b) a shell encapsulating said core; and (c) a coating encapsulating said shell, wherein said coating is not immunoreactive. In some embodiments, the metallic core is a silver nanoparticle. In yet another aspect, provided herein are methods of producing encapsulated nanoparticles, the method include the steps of: (a) providing a metallic core; (b) encapsulating said core with a shell: and (c) encapsulating said shell with a coating.

In another aspect, provided herein are methods of dual energy x-ray imaging of tissue (e.g., breast tissue) in a subject (e.g., a human), the methods include the steps of: (a) administering to said subject a metal contrast agent (e.g., a stabilized metal nanoparticle contrast agent or an encapsulated metal nanoparticle); (b) acquiring an image at a low energy spectrum; and (c) acquiring an image at a high energy spectrum.

Unless otherwise defined, all technical and scientific terms used herein have the same meaning as commonly understood by one of ordinary skill in the art to which this invention belongs. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

$S_D$ is given by a weighted subtraction of the high and low signal intensities.

Figure 4:
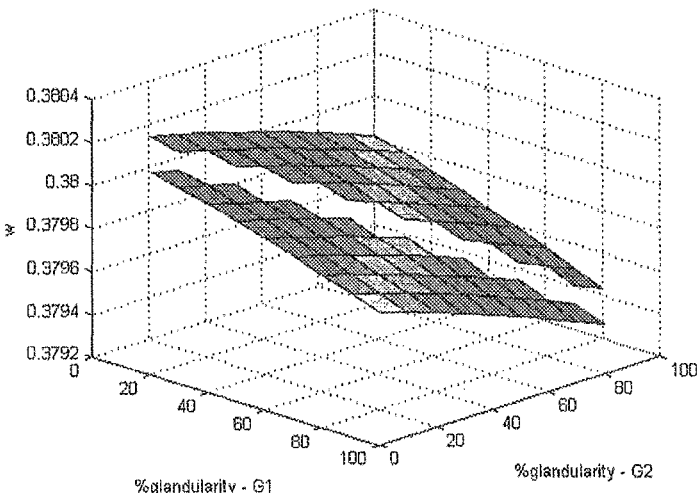

FIG. 4. Weighting factors calculated for SI (low) and S2 (high) of Example 1.

Figure 5:
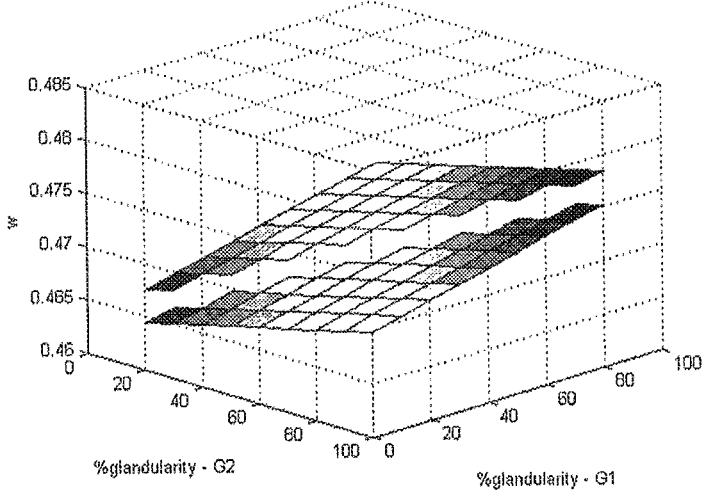

FIG. 5. Weighting factors calculated for S2 (low) and S3 (high) of Example 1.

Figure 6:
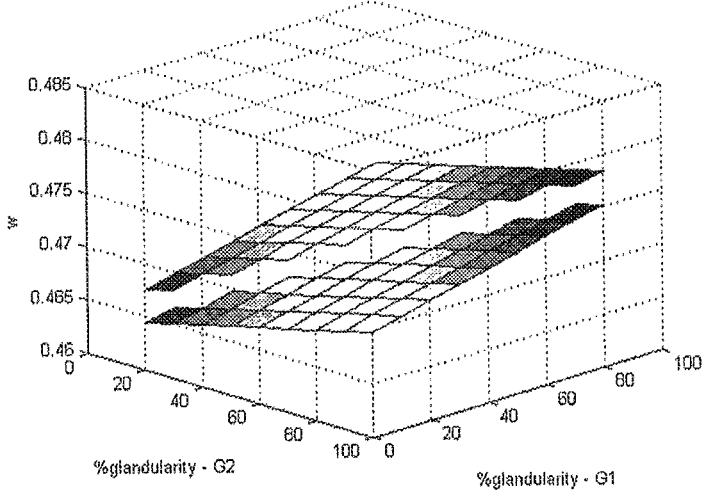

FIG. 6. Transmission electron micrograph (TEM) of the colloidal silver nanoparticles synthesized using the Brust method in water. The particles have been stabilized using a polyethylene glycol surface chain.

Figure 7:
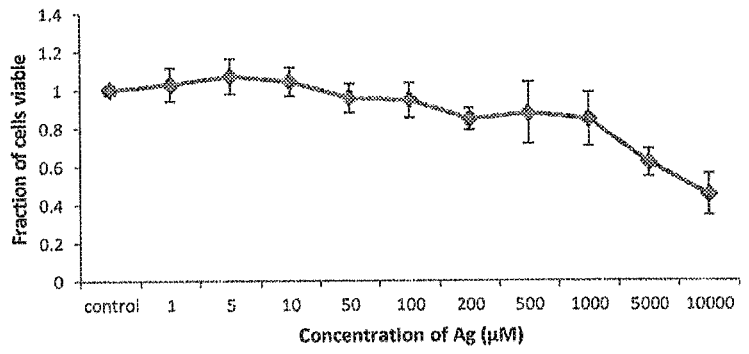

FIG. 7. Cellular toxicity of Silver nanoparticles (AgNP) in T6-17 cells after 24-hour incubation.

Figure 8:
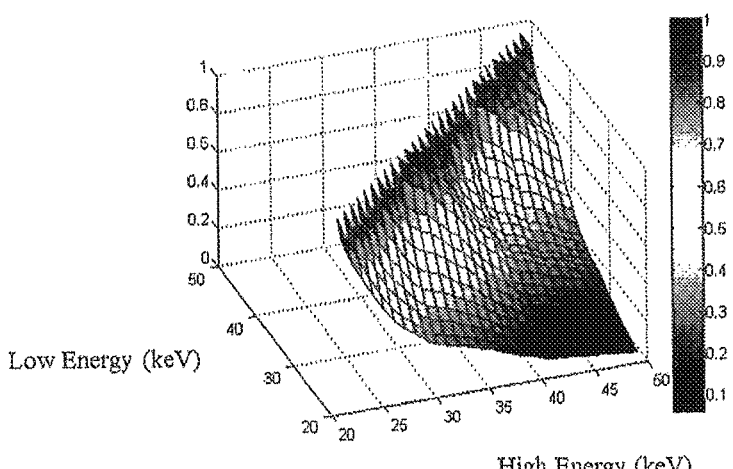

FIG. 8. W calculated for energy combinations ranging from 20 to 50 keV. Values ranged from 0 to 1.

Figure 9:
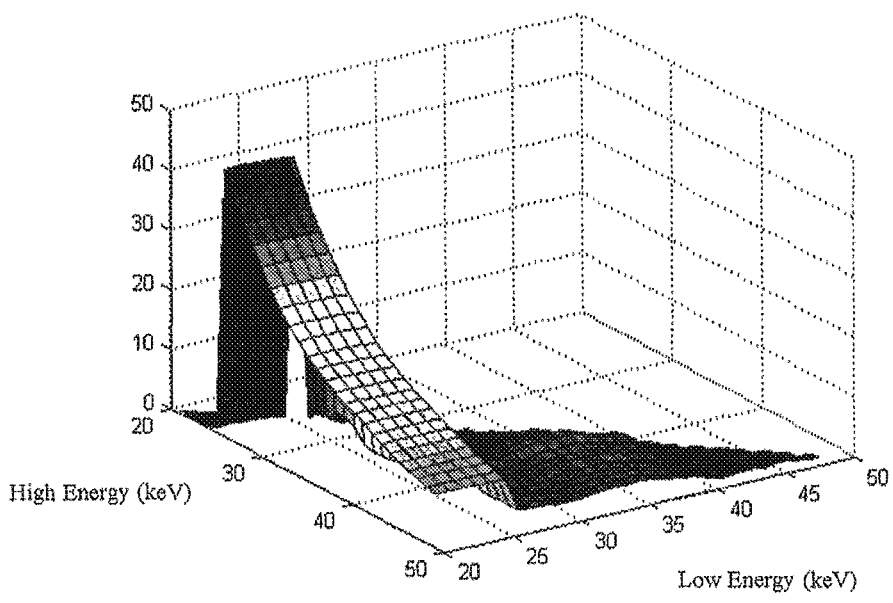

FIG. 9. SC calculated for silver at energy pairs between 20 and 50 keV. The maximum contrast of 45 a.u. occurs at a low energy of 21 keV, and a high energy of 26 keV.

Figure 10:
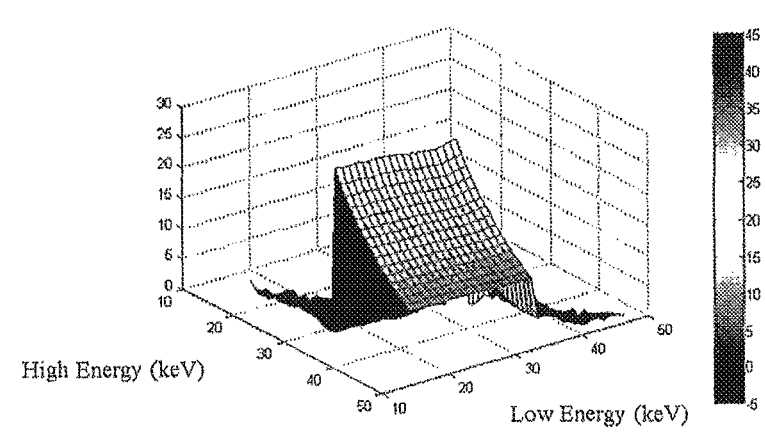

FIG. 10. SC calculated for iodine at energy pairs between 15 and 50 keV. The maximum achievable contrast is 33% lower than that of silver.

Figure 11:
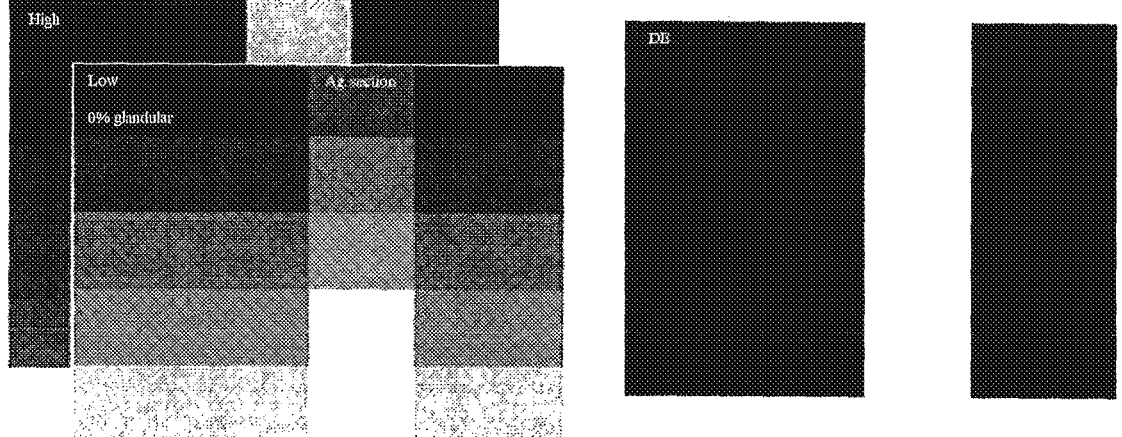

FIG. 11. High (26 keV)- and Low (21 keV)-energy images of a step phantom with a section of embedded Ag. The images are subtracted using the pre-calculated weighting factor to yield the DE image shown on the right.

Figure 12:
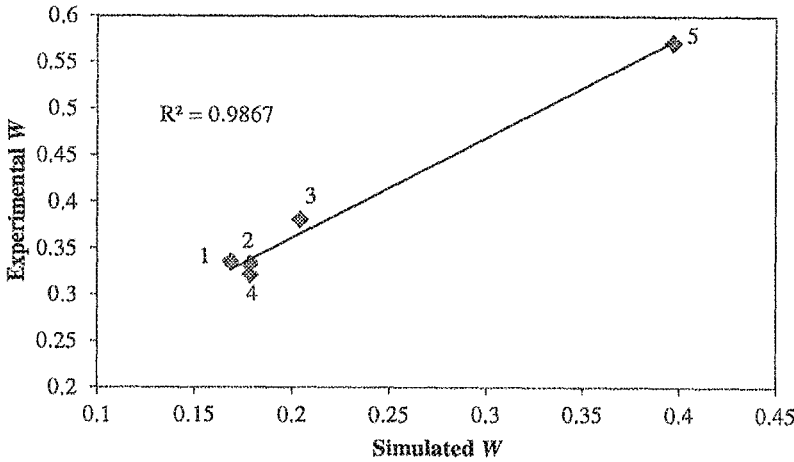

FIG. 12. The experimental and simulated values of W show excellent agreement.

Figure 13:
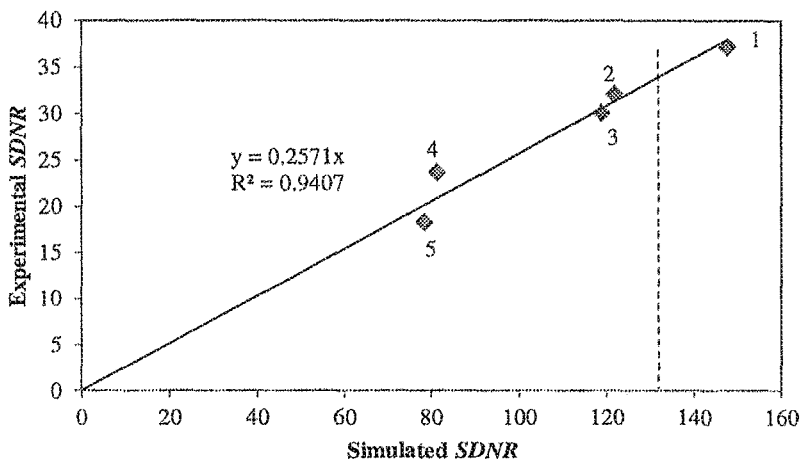

FIG. 13. Correlation between simulated and experimental SDNR values. The data shows excellent agreement between the simulated and experimentally-obtained values, with the optimization point providing the maximum in both. The red dashed line indicates the maximum simulated SDNR for iodine, calculated under the same constraints.

Figure 14:
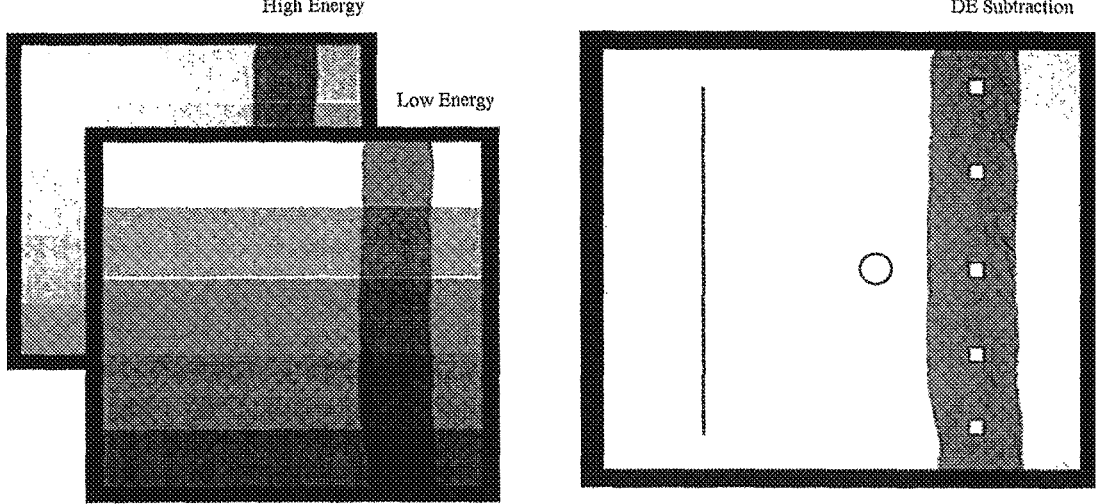

FIG. 14. Low- and high-energy images along with the DE subtraction of a 4 cm step phantom with a silver foil emulating an areal concentration of 25 mg/cm$^2$. The artifacts present in the image of the foil arise from physical imperfections in the material.

Figure 15:
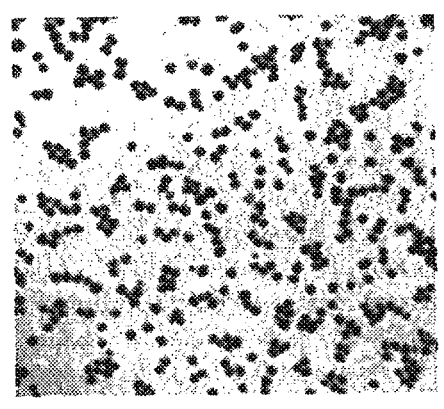

FIG. 15. Transmission electron micrograph (TEM) image of the PVP-coated silver nanoparticles FIG. 16. TEM image of silica-coated silver nanoparticles.

Figure 17:

FIG. 17. TEM image of PEG-stabilized silica-coated nanoparticles.

Figure 18:
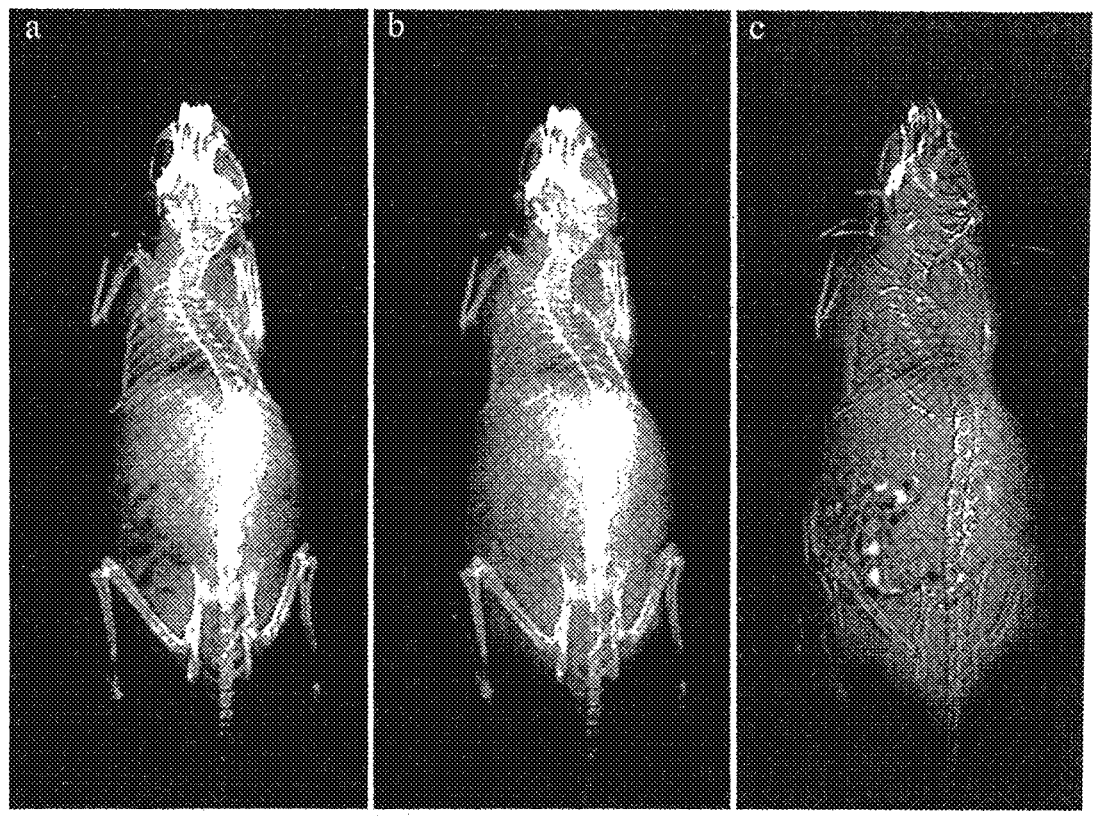

FIG. 18. LE (a), HE (b), and DE (c) images of a mouse prior to injection of PEG-SiAg nanoparticles.

Figure 19:
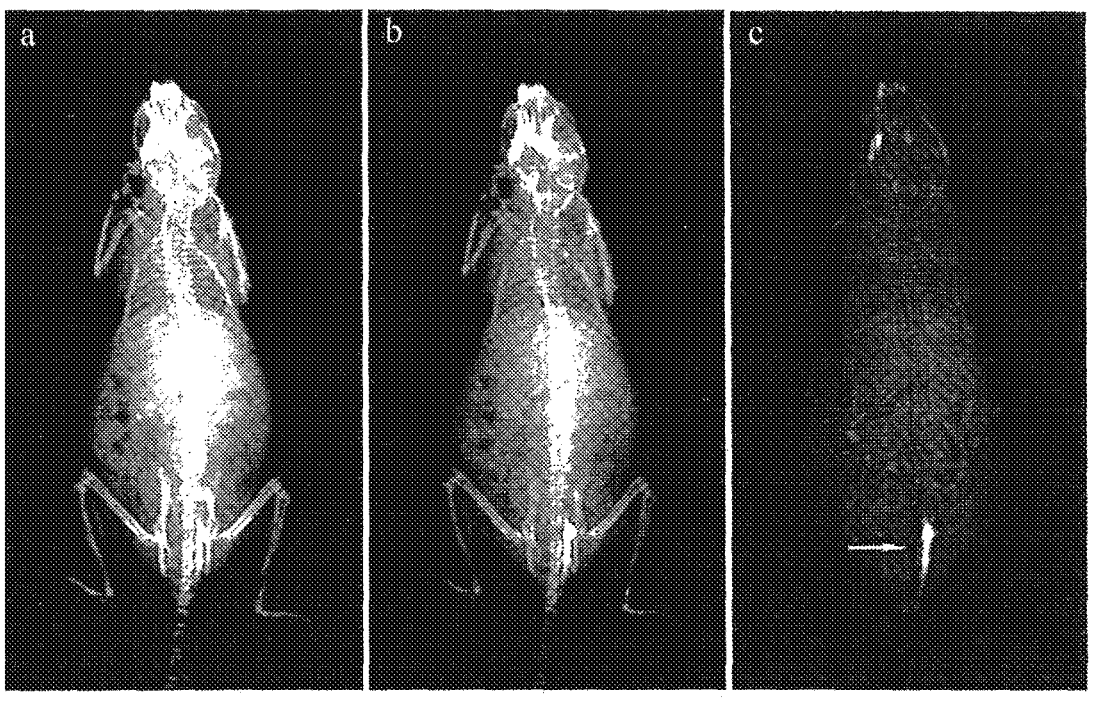

FIG. 19. LE (a), HE (b), and DE (c) images of a mouse after injection of PEG-SiAg nanoparticles via the tail vein.

Figure 20:
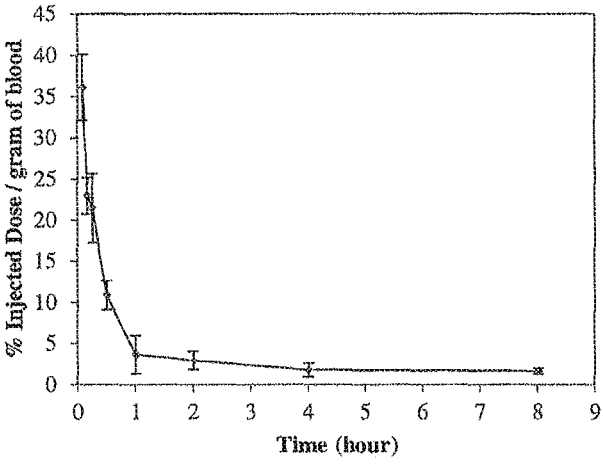

FIG. 20. Blood clearance of PEG-SiAg nanoparticles after intravenous injection into female mice.

Figure 21:
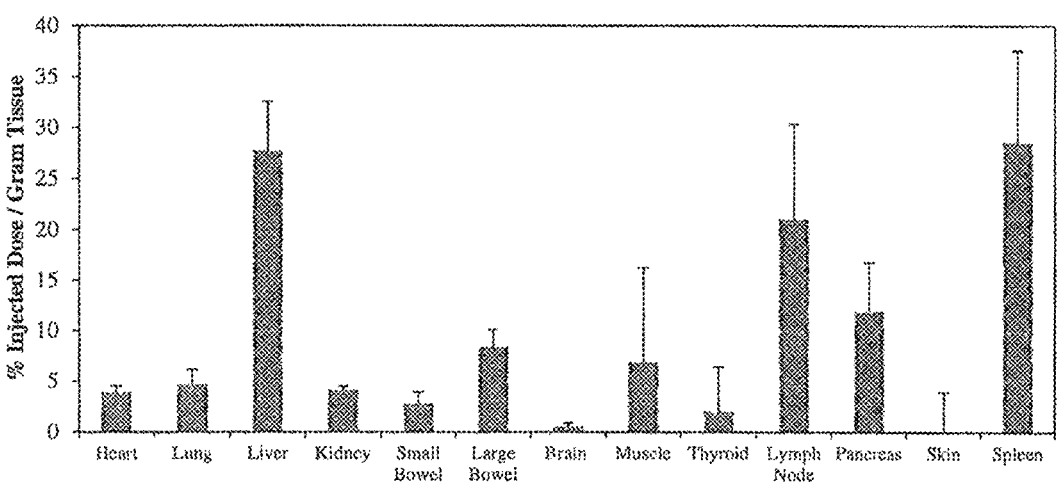

FIG. 21. Biodistribution of PEG-SiAg nanoparticles 24 hours after intravenous injection into female mice.

Figure 22:
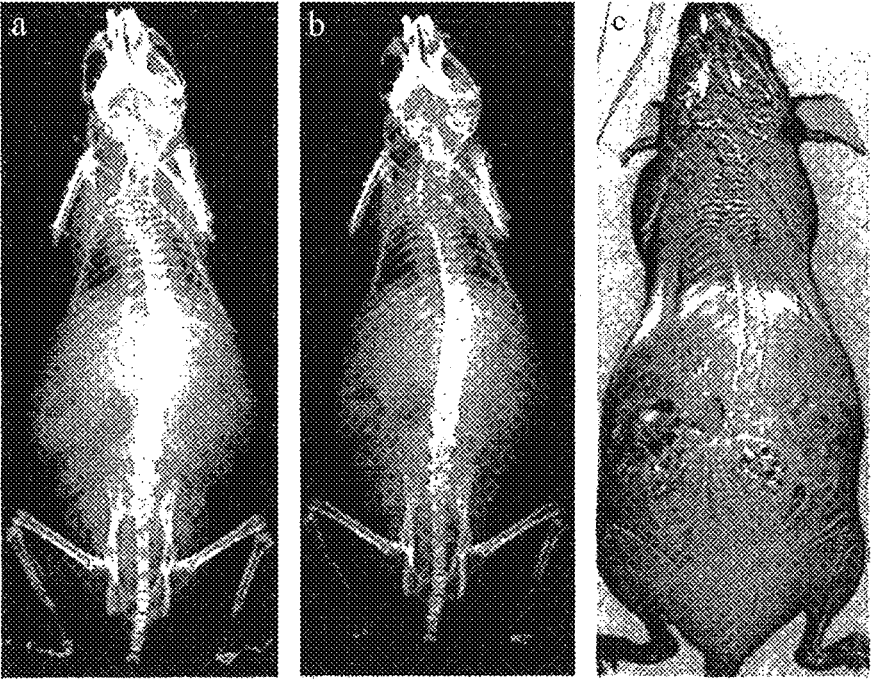

FIG. 22. LE (a), HE (b), and DE (c) images of a mouse after intraperitoneal injection of PEG-SiAg nanoparticles into female mice.

Figure 23:
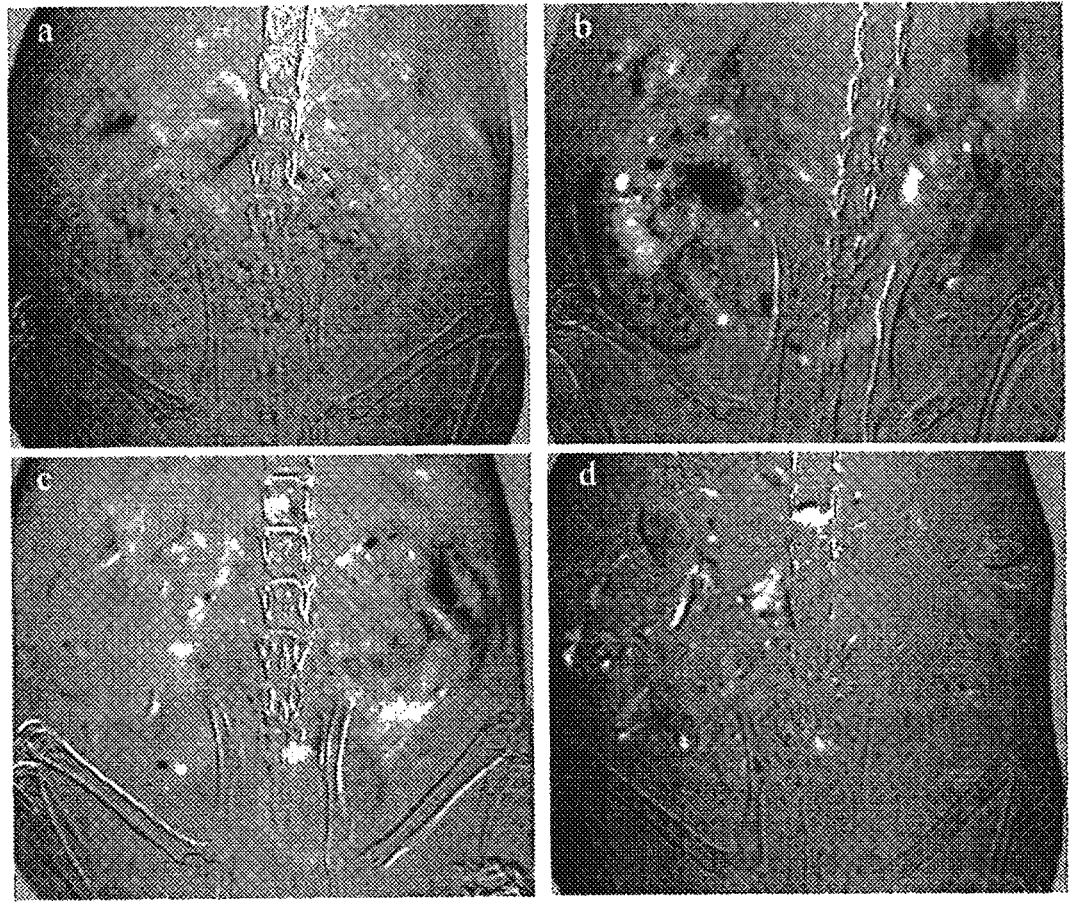

FIG. 23. Progression of the contrast as a result of the PEG-SiAg nanoparticles in the DE images (a) 5 minutes, (b) 20 minutes, (c) 40 minutes, and (d) 50 minutes post-injection.

Figure 24:
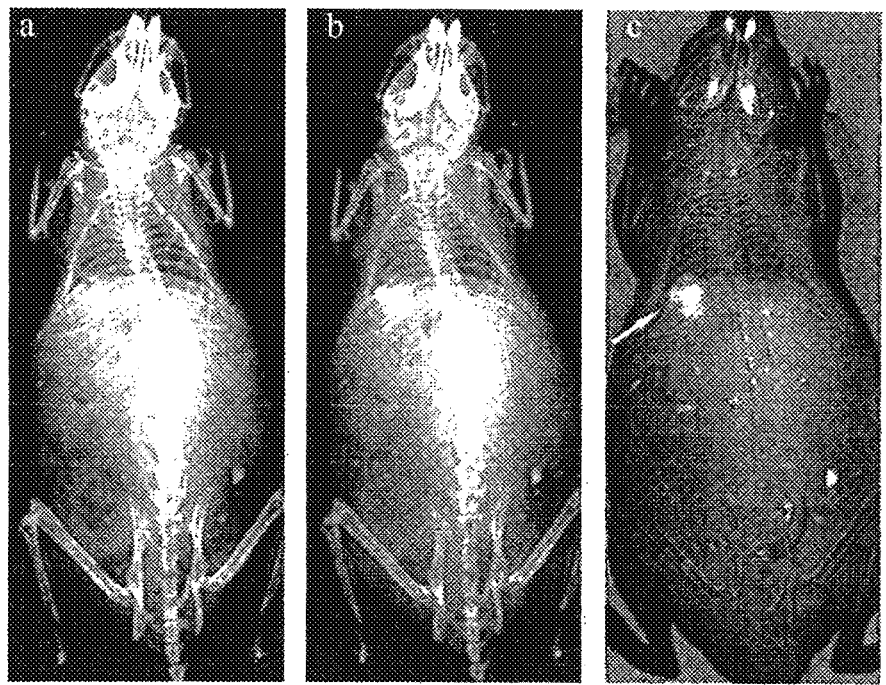

FIG. 24. LE (a), HE (b), and DE (c) images of a mouse after subcutaneous injection of PEG-SiAg nanoparticles into female mice

DETAILED DESCRIPTION OF THE INVENTION

In one aspect, provided herein are contrast agents for x-ray imaging, the contrast agents comprising stabilized metal nanoparticles. Also provided herein are methods of x-ray imaging of tissue (e.g., breast tissue) in a subject (e.g. a human), comprising administering any of the stabilized metal nanoparticles described herein.

In some embodiments, the stabilized metal nanoparticle contrast agents avoid cytotoxicity and/or immunoreactivity. In some embodiments, the contrast agents lack an active targeting agent to act as a blood pool imaging agent. In some embodiments, the contrast agents comprise a targeting ligand or targeting agent that targets the agent to one or more tumors or cell types, for example, cancer cells such as breast cancer cells or tumor targets such as tumor-associated macrophages (TAMs) or endothelial cells. According to at least one embodiment, the targeting ligand or targeting agent may comprise an antibody, antibody fragment, protein, peptide, small molecule (e.g., sugar), or an aptamer.

According to at least one embodiment, the metal nanoparticles are selected from the group consisting of silver, rhodium, palladium, cadmium, bismuth, zirconium, tin, gold, platinum, and molybdenum. In at least one embodiment, the metal nanoparticles are silver nanoparticles.

In some embodiments, the metal nanoparticles are synthesized using the Brust method in water. In some embodiments, the metal nanoparticles have a mean diameter of about 4±2 nm.

In some embodiments, the metal nanoparticles are stabilized with polyethylene glycol (PEG). In some embodiments, the PEG has a molecular weight (Mw) of about 5000. In some embodiments, the molar ratio between the PEG stabilizing ligand and silver is about 1.5:1.

In another aspect, provided herein are composition of encapsulated nanoparticles, an encapsulated nanoparticle includes: (a) a metallic core; (b) a shell encapsulating said core; and (c) a coating encapsulating said shell, wherein said coating is not immunoreactive. In some embodiments, the metallic core is selected from silver, rhodium, palladium, cadmium, bismuth, zirconium, tin, gold, platinum, and molybdenum nanoparticles. In at least one embodiment, the metallic core is a silver nanoparticle. In yet another aspect, provided herein are methods of producing encapsulated nanoparticles, the method include the steps of: (a) providing a metallic core; (b) encapsulating said core with a shell; and (c) encapsulating said shell with a coating.

The core will generally have an average diameter from about 0.5 nm to about 100 nm. In preferred embodiments, the core will have an average diameter from about 5 nm to about 50 nm. The shell will generally have average thickness from about 5 nm to about 150 nm. In preferred embodiments, the shell will generally have average thickness from about 10 nm to about 150 nm. The encapsulated nanoparticles core and the shell will generally have average diameter from about 10 nm to about 1000 nm. In preferred embodiments, the encapsulated nanoparticles will generally have an average diameter from about 15 nm to about 200 nm.

In preferred embodiments, the shell comprises silica. Materials other than silica are contemplated as suitable materials for the shell provided they can be bound strongly to the surface of the core. For example, the shell can be composed of a hydrophobic polymer (e.g., poly(lactic-co-glycolic acid (PLGA) or polylactic acid (PLA)), or oils (e.g., soy bean oil).

In preferred embodiments, the coating comprises a PEG-polycaprolactone (PCL) diblock copolymer PEG-PCL. Materials other than PEG-PCL are contemplated as suitable materials for the coating provided they do not elicit an immune response. For example, other suitable diblock copolymers, include, but are not limited to, PEG-PLA or PEG-PLGA; suitable amphiphilic polymers include, but are not limited to, polyvinyl alcohol (PVA) or an amine modified or unmodified poly(maleic anhydride-alt-1-octadecene) (PMAL). The PMAL may be modified with an amine, such as, for example, 3-(dimethylamino) propylamine. Other suitable materials include, but are not limited to, phospholipids or PEG-phospholipids.

The polymer or polymer block may be of any molecular weight, and may be branched or unbranched. For polyethylene glycol, the preferred molecular weight is between about 1 kDa and 15 about 100 kDa (the term "about"

indicating that in preparations of polyethylene glycol, some molecules will weigh more, some less, than the stated molecular weight) for ease in handling and manufacturing. Other sizes may be used. For example, the polyethylene glycol may have an average molecular weight of about 200, 500, 1000, 1500, 2000, 2560, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. It will also be appreciated, that for the block copolymers used herein the blocks can have different block sizes, e.g., PEG(2 kDa)-PCL(2.7 kDa), PEG(4 kDa)-PCL(3 kDa), PEG(5 kDa)-PCL(5 kDa) and PEG(5 kDa)-PCL(4 kDa).

In another aspect, provided herein are methods of dual energy x-ray imaging of tissue (e.g., breast tissue) in a subject (e.g. a human), the methods include the steps of: (a) administering to said subject a metal nanoparticle contrast agent (e.g., a stabilized metal nanoparticle, such as, for example, a silver nanoparticle contrast agent or an encapsulated metal nanoparticle, such as, for example, an encapsulated silver nanoparticle); (b) acquiring an image at a low energy spectrum; and (c) acquiring an image at a high energy spectrum. In some embodiments, acquiring an image at a low energy spectrum comprises filtering with a filter selected from the group consisting of a molybdenum filter, a rhodium filter, a silver filter and combinations thereof. In some embodiments, acquiring an image at a high energy spectrum comprises filtering with a filter selected from the group consisting of a tin filter, an aluminum filter, a copper filter and combinations thereof.

While the methods provided herein are exemplified for breast imaging using silver, they are not limited to such. Other imaging modalities are contemplated, such as without limitation, arthrography, angiography, venography. Furthermore, the use of any metal suitable as a contrast agent is contemplated, for example, other suitable metals include, but are not limited to, rhodium, palladium, cadmium, bismuth, zirconium, tin, gold, platinum or molybdenum.

Pharmaceutical compositions comprising any of the aforementioned contrast agents or encapsulated nanoparticles are embraced herein.

Embodied herein are contrast agents or encapsulated nanoparticles as described herein and pharmaceutical compositions thereof. It will be appreciated that the agents and compositions, according to the methods of the present invention, may be administered using any amount and any route of administration effective for imaging the desired tissue. The exact amount required will vary from subject to subject, depending on the species, age, and general condition of the subject, the particular contrast agent, its mode and/or route of administration, and the like. The contrast agents or encapsulated nanoparticles are preferably formulated in dosage unit form for ease of administration and uniformity of dosage. The expression "dosage unit form" as used herein refers to a physically discrete unit of contrast agent or encapsulated nanoparticles appropriate for the patient to be imaged. It will be understood, however, that the total daily usage of the contrast agents or encapsulated nanoparticles and compositions of the present invention will be decided by the attending physician within the scope of sound medical judgment. The specific level for any particular patient or organism will depend upon a variety of factors including the tissue being imaged; the activity of the specific agent employed; the specific composition employed; the age, body weight, general health, sex and diet of the patient; the time of administration, route of administration, and rate of excretion of the specific agent employed; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracistemally, intravaginally, intraperitoneally, subcutaneously, intradermally, intra-ocularly, topically (as by powders, ointments, or drops), buccally, as an oral or nasal spray, or the like, depending on the tissue being imaged. In certain embodiments, the contrast agents or encapsulated nanoparticles are administered orally or parenterally.

In some embodiments of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In some embodiments of the present invention, the active ingredient is formulated in a capsule. In accordance with this embodiment, the compositions of the present invention comprise, in addition to the active compound and the inert carrier or diluent, a hard gelatin capsule.

In some embodiments, the pharmaceutical compositions are administered by intravenous, intra-arterial, subcutaneous or intra-muscular injection of a liquid preparation. Suitable liquid formulations include solutions, suspensions, dispersions, emulsions, oils and the like. In some embodiments, the pharmaceutical compositions are administered intravenously and are thus formulated in a form suitable for intravenous administration. In some embodiments, the pharmaceutical compositions are administered intra-arterially and are thus formulated in a form suitable for intra-arterial administration. In some embodiments, the pharmaceutical compositions are administered intra-muscularly and are thus formulated in a form suitable for intra-muscular administration.

In some embodiments, the pharmaceutical compositions are administered topically to body surfaces and are thus formulated in a form suitable for topical administration. Topical formulations include, in some embodiments, gels, ointments, creams, lotions, drops and the like.

In some embodiments, the pharmaceutical composition is administered as a suppository, for example a rectal suppository or a urethral suppository. In some embodiments, the pharmaceutical composition is administered by subcutaneous implantation of a pellet. In some embodiments, the pellet provides for controlled release of active agent over a period of time.

In some embodiments, the active compound is delivered in a vesicle, e.g., a liposome.

In other embodiments, carriers or diluents used in methods of the present invention include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In some embodiments, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In some embodiments, the compositions further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., aspartame, citric acid), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

Also contemplated are particulate compositions coated with polymers (e.g., poloxamers or poloxamines) and the contrast agents or encapsulated nanoparticles coupled to antibodies directed against tissue-specific receptors, ligands or antigens or coupled to ligands of tissue-specific receptors.

The term "subject" as used herein can be any suitable mammal, including primates, such as monkeys and humans, horses, cows, cats, dogs, rabbits, and rodents such as rats and mice. In one embodiment, the mammal to be imaged in the methods provided herein is a human.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art.

All sequence citations, accession numbers, references, patents, patent applications, scientific publications or other documents cited are hereby incorporated by reference.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

EXAMPLES

Example 1

Silver nanoparticles are a suitable alternative to iodine in dual-energy tissue, such as breast, x-ray imaging. Dual-energy imaging involves acquiring images at two distinct energy spectrums (low and high). Weighting factors are then applied to create an image where the contrast between background tissues has been suppressed. Silver (Ag) represents an attractive contrast material due to its favorable x-ray attenuation properties (k-edge of 25.5 keV). Silver is favorable for both dual-energy and temporal subtraction methods. Simulations using polychromatic spectra show that silver can provide similar, if not better, contrast to iodine. Spherical Ag nanoparticles with an average diameter of 4 ±2 nm were synthesized using the Brust method (Brust M., el al., Synthesis of thiolderivatized gold nanoparticles in a 2-phase liquid-liquid system. J. Chem. Soc. Chem. Commun. (1994) 801-802, which is hereby incorporated by reference in its entirety) in water. The particles were surface stabilized with polyethylene glycol and showed little cellular toxicity in T6-17 fibroblast cells. Silver nanoparticles represent an exciting avenue as a novel dual-energy, x-ray tissue (e.g., breast) imaging agent.

Figure 1:
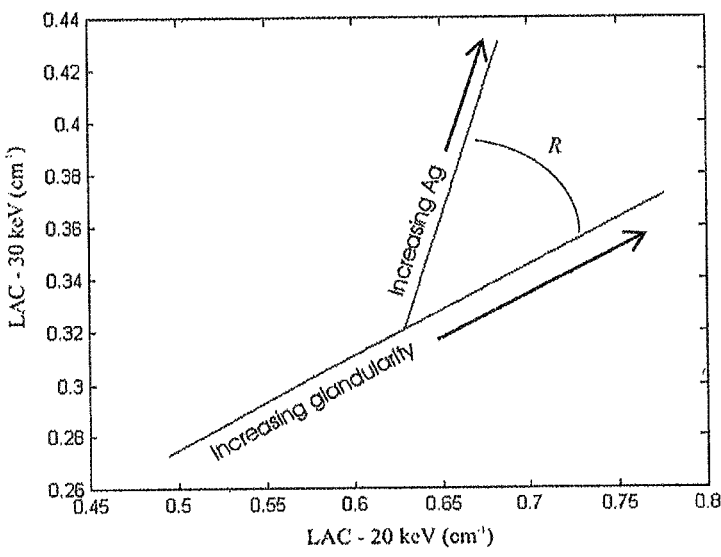
FIG. 1. Two dimensional map of Linear attenuation coefficients (LAC) for variations of glandularity and concentration of silver, the metric R was defined as the angle between the two linear fits.
Figure 2:
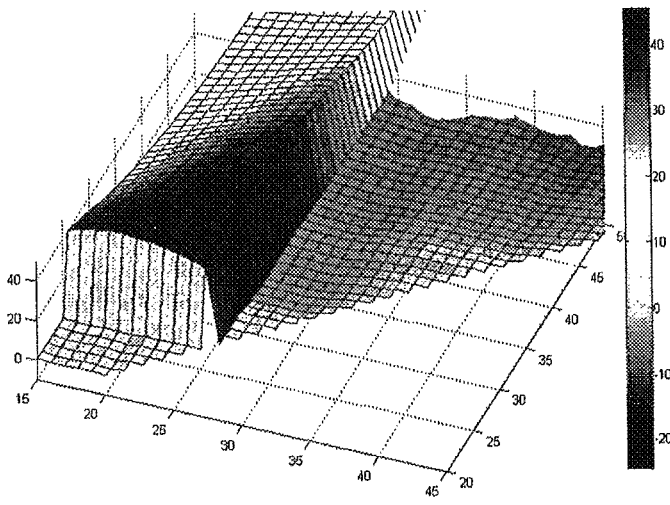
FIG. 2. Surface plot of R for various combinations of low- and high-energy pairs. A maximum occurs at (20, 30) keV providing an R of 44°.

Theoretical Simulations:

Monoenergetic analysis: A monoenergetic analysis was first performed to identify candidate combinations of low (LE) and high (HE) energies. Linear attenuation coefficients (LAC) were calculated for various admixtures of glandular and adipose tissues ranging from 0 to 100% glandular. Separately, the LAC were calculated for a 50% glandular, 50%) adipose composite with increasing concentrations of contrast material. Mass attenuation coefficients needed for this calculation were obtained from the NIST XCOM online physics database (National Institute of Standards and Technology (NIST) Physical Measurement Laboratory. XCOM: Photon Cross Sections Database.). Energy pairs ranging from 15 to 45 keV (in 1 keV intervals) were studied. For each energy-pair, two-dimensional maps of linear attenuation coefficients for tissue were calculated in terms of glandularity and concentration of silver (see FIG. 1). Linear relationships were observed for both variables. The metric R was defined as the angular separation between these two linear fits.

An energy pair of (20, 30) keV was identified to maximize R (44°) using a silver contrast agent. A similar calculation for iodine showed that R was maximum at an energy pair of (30,40) keV with a value of 39°. These energy pairs were further studied with polychromatic spectral analysis.

Polychromatic Spectra: Tungsten polychromatic spectra were designed using the interpolating method of Boone et al. (*Molybdenum, rhodium, and tungsten anode spectral models using interpolating polynomials with application to mammography*, Med Phys, 24; 12 (1997) 1863-1874, which is hereby incorporated by reference in its entirety). Hundreds of combinations of kVp and filter materials were tested until three spectra with mean energies of roughly 20 (S1), 30 (S2) and 40 keV (S3) were chosen, as shown in Table 1. It is expected that a spectral pair of SI, S2 would be more beneficial to a silver contrast agent compared to iodine while a spectral pair of S2, S3 would be better suited to an iodinated contrast agent.

TABLE 1

| Parameters used for the simulation of the 3 spectra with various average energies. | | | |
|---|---|---|---|
| | KVp | Filter Combination[§] | Average Energy (keV) |
| S1 | 32 | 80 μm Ag | 21.6 |
| S2 | 45 | 0.2 cm Al | 30.0 |
| S3 | 49 | 0.03 cm Cu | 38.0 |

[§]Abbreviations used for the filter: Ag (silver), Al (aluminum), Cu (copper)

Weighting Factors: For each spectrum, the transmission through 1 cm of tissue of 5 varying breast tissue composition (0% to 100% glandular) was calculated. A thickness of 1 cm was chosen as an initial starting point for our calculations. The transmission was then converted to signal intensity (S) given by:

$$S = \ln\left(\sum_{E=0}^{kVp} E \times I_E \times e^{-\mu_E t}\right) (\text{SEQ equation}\backslash n * MERGEFORMAT 1)$$

where E is the energy in keV, $I_E$ is the incident photon fluence (photons/mm2) at that energy, $\mu_E$ is the linear attenuation coefficient of the breast tissue composition at that energy E, and t is the thickness of tissue. This formulation assumes that an ideal energy-integrating detector is used. The dual-energy signal (SD) was defined as the weighted subtraction of the low- and high-energy SI:

$$S_D = S_{HE} - w \times S_{LE} (\text{SEQ equation}\backslash n * MERGEFORMAT 2)$$

Figure 3:
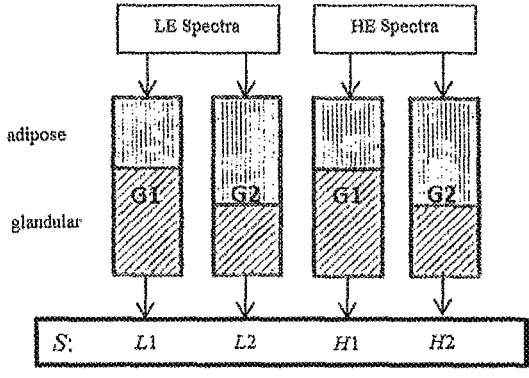
FIG. 3. Schematic setup for determining the weighting factor for a given pair of tissue glandularities (G1, G2). A weighting factor is chosen so as to equate the $S_D$ of the two materials.

For a given pair of tissue glandularities (see FIGS. 3, G1 and G2), a weighting factor was determined such that the DE signal from G1 was equal to that of G2.

$$S_D(G1) =$$

$$S_D(G2) \rightarrow w = \frac{H1 - H2}{L1 - L2} (\text{SEQ equation}\backslash n * MERGEFORMAT 3)$$

Thus, in a DE image no contrast would be observed between these two tissue types using this calculated weighting factor.

The weighting factor needed to suppress various combinations of tissue glandularities are shown for a high/low spectral combination of S0, SI (FIG. 4) and SI, S2 (FIG. 5). The weighting factor is relatively invariant with tissue composition, implying that for a given spectral pair of low-and high-energy beams, it should be possible to effectively null the contrast between the underlying tissue structures in the breast.

Contrast Calculation: The calculated values of w were used to determine DE signals for background tissue (50% adipose, 50% glandular) and contrast enhanced tissue (50% adipose, 50% glandular 30 1 mg/mL of contrast material). The contrast (C) was calculated as the difference in $S_D$ of tissue with and without contrast material. Values of C using silver, iodine and various low/high spectral pairs are tabulated in Table 2. The data correlates well with those predicted by monoenergetic calculations.

The contrast observed for each contrast material is greater when using the spectral pair that brackets the k-edge of that material. The contrast observed for silver is greater when using the (S1, S2) spectral pair. Conversely, the contrast observed for iodine is greater when using the (S2, S3) spectral pair.

The maximum contrast observed for silver is greater than that of iodine. By comparing the spectral pairs that best suited each material, it was found that the contrast observed for silver was roughly twice that of iodine.

These results demonstrate the significant potential of silver as a contrast material for dual-energy breast x-ray imaging.

TABLE 2

| Signal Differences tabulated for silver and iodine using various low-and high-energy spectral combinations. | | |
|---|---|---|
| | Spectral Combinations | |
| C (Digital Units) | Low E: $S_1$ High E: $S_2$ | Low E: $S_2$ High E: $S_3$ |
| Silver | 20.8 ± 0.003 | 7.44 ± 0.08 |
| Iodine | 9.88 + 0.004 | 11.70 ± 0.05 |

Silver Nanoparticles:

Silver nanoparticles (AgNP) have been synthesized using the Brust (*Synthesis of thiolderivatized gold nanoparticles in a 2-phase liquid-liquid system*, J. Chem. Soc. Chem. Commun. (1994) 801-802) method in water. This is preferred over the Turkevich method as it provides a more reliable size distribution of particles from batch to batch. FIG. 6 shows a transmission electron micrograph (TEM) of the synthesized particles. Analysis of the size distribution yielded a mean diameter of 4±2 nm. Initial analysis showed two populations of nanoparticles present which accounts for the high standard deviation in mean diameter. The AgNP were surface stabilized using polyethylene glycol (PEG, $M_w$=5000) to improve solubility in cell media and phosphate buffered solutions. A molar ratio of 1.5:1 was used between the PEG stabilizing ligand and silver.

The cellular toxicity of the stabilized AgNP was measured in T6-17 fibroblast cells using the MTT assay. FIG. 7 shows the relationship between concentration of Ag in AgNP and percent cell viability after 24 hour incubation. Compared to a sham treated control, total cell viability of 50% was maintained at an Ag concentration of 10 mM (roughly 1 mg Ag/mL). These results show marked improvement over cell viability studies using AgNP in the literature (Hussain S., et al. *In Vitro Toxicity of nanoparticles in BRL 3A rat liver cells*, Toxicology in Vitro (2005) 975-983; Navarro E., et al. *Toxicity of Silver Nanoparticles to Chlamydomonas reinhardtii*, Environmental Science and Technology (2008) 8959-8964).

Silver is a novel imaging agent for dual-energy tissue (e.g., breast) x-ray imaging. Monoenergetic analysis of linear attenuation coefficients showed that compared to iodine it is possible to achieve a greater separation between tissue with and without contrast when silver is used. These results were corroborated by polyenergetic spectra simulation where silver showed up to twice the radiographic contrast of iodine. These simulations demonstrated that within the mammographic energy range, silver is able to offer comparable, if not greater DE contrast to iodine.

Furthermore, work has been completed on the synthesis and testing of AgNP. Spherical AgNP (d=4 ±2 nm) were synthesized using the Brust method, and stabilized with PEG surface ligands. Little cellular toxicity was observed in cells for silver concentrations up to 1 mg/mL.

Example 2

Contrast-enhanced dual-energy (CEDE) breast x-ray imaging encompasses an emerging group of modalities that aim to provide quantitative functional information together with high-resolution anatomical data. The unique combination of information in a single imaging procedure represents a powerful breast imaging tool for morphological and vascular characterization of breast lesions. DE imaging is used to increase the contrast of radiographic imaging agents by suppressing the anatomical signal variation in the body. In the breast, this involves the suppression of the signal variation that arises from differences in soft tissue (adipose and glandular) composition across the image. By reducing the effect of this soft tissue noise, it is then possible to segment and quantify the signal from an exogenous imaging agent. In CEDE imaging, two distinct energy spectrums (low- and high-) are used to quantify the variation in attenuation with energy. By employing a contrast agent whose linear attenuation k-edge lies within the energy ranges used, it is possible to separate its signal from the surrounding tissue.

Traditionally, CEDE breast imaging has been employed with an iodinated contrast agent. These agents do, however, possess several limitations that have fueled the research for improved imaging agents. The non-specific nature of the contrast agent results in random vascular permeation, and their relatively low molecular weight facilitates rapid renal clearance. Because these agents lack an appropriate layer of surface biomolecules to prevent the non-specific binding of blood serum proteins, the percentage of the injected dose that reaches the tumor site is low. Perhaps most importantly, iodinated contrast agents were designed for radiographic imaging procedures at much higher x-ray energy ranges than those used in breast imaging. Thus, a more radiographically-suited breast imaging agent is proposed.

Silver represents an attractive base material due to the central location of its k-edge (25.5 keV in the mammographic clinical energy range. This Example presents the DE subtraction methodology needed to remove soft-tissue contrast while maintaining the signal from a silver imaging agent.

Methods

Imaging Framework

The signal intensity from either the low- or high-energy image can be expressed in terms of the various attenuation coefficients and corresponding thicknesses of materials present in the beam path. In the simplistic case of a monoenergetic x-ray source, these signal intensities can be formulated using the Beer-Lambert law as:

$$\ln(I) = \ln(I_0) + \left(-\sum \mu t\right) \qquad (1)$$

where $I_0$ is the initial photon fluence, $\mu$ is the linear attenuation coefficient, t is the thickness of the material. In the case of dual-energy breast x-ray imaging, the principal materials that contribute to the attenuation of the x-ray photons are adipose (a), glandular (g) and contrast agent (c). Thus Equation 1, can be rewritten with these three materials for both low-(L) and high-(H) energy photons.

$$\ln\left(I^L\right) = \ln\left(I_0^L\right) + \left(-\mu_a^L t_a - \mu_g^L t_g - \mu_c^L t_c\right) \qquad (2)$$

$$\ln\left(I^H\right) = \ln\left(I_0^H\right) + \left(-\mu_a^H t_a - \mu_g^H t_g - \mu_c^H t_c\right) \qquad (3)$$

If we then assume that the total thickness of tissue, t can be expressed as the sum of adipose and glandular thicknesses:

$$t = t_a + t_g \qquad (4)$$

we can substitute out $t_a$ in Equations 2 and 3. Thus the signal intensity at each energy level can be described in terms of the total thickness of tissue, the amount of glandular tissue, and the amount of contrast material:

$$\ln\left(I^L\right) = \ln\left(I_0^L\right) - \mu_a^L t + t_g\left(\mu_a^L - \mu_g^L\right) - \mu_c^L t_c \qquad (5)$$

$$\ln\left(I^H\right) = \ln\left(I_0^H\right) - \mu_a^H t + t_g\left(\mu_a^H - \mu_g^H\right) - \mu_c^H t_c \qquad (6)$$

The DE signal intensity ($SI_{DE}$) can be expressed as a weighted (W) subtraction between the high- and low-energy signal intensities.

$$SI^{DE} = \ln\left(I_0^H\right) - W \times \ln\left(I_0^H\right) + t \times \left[-\mu_a^H + W \times \mu_a^L\right] + \qquad (7)$$
$$t_g \times \left[\left(\mu_a^H - \mu_g^H\right) - W \times \left(\mu_a^L - \mu_g^L\right)\right] + t_c \times \left(-\mu_c^H + W \times \mu_c^L\right)$$

$SI_{DE}$ can be broken down into three major components. The first component, $$\ln\left(I_0^H\right) - W \times \ln\left(I_0^H\right) + t \times \left[-\mu_a^H + W \times \mu_a^L\right]_z,$$

is a combination of the initial photon fluence and total thickness of the breast. This component can be assumed to be constant across the image and thus provides an offset to $SI_{DE}$. The second component, $$t_g \times \left[\left(\mu_a^H - \mu_g^H\right) - W \times \left(\mu_a^L - \mu_g^L\right)\right],$$

describes the relationship between $SI_{DE}$ and the amount of glandular tissue in the beam. By choosing W as:

$$W = \frac{\mu_a^H - \mu_g^H}{\mu_a^L - \mu_g^L} \qquad (8)$$

we can eliminate this dependence. Thus the only remaining term that varies across the image is the third component $$t_c \times \left[ -\mu_c^H + W \times \mu_c^L \right].$$

This component quantifies the linear relationship between $SI_{DE}$ and the thickness of contrast material. The contrast, $S_{C_t}$ can be defined as the change in $SI_{DE}$ with respect to $t_c$:

$$\frac{d\left(SI^{DE}\right)}{d(t)} = S_C = -\mu_c^H + \frac{\mu_a^H - \mu_g^H}{\mu_a^L - \mu_g^L} \times \mu_c^L \qquad (9)$$

Monoenergetic Simulation Testing

The subtraction method was tested using a computer-simulated, monoenergetic x-ray acquisition. Photons of a single energy are passed through a 5 cm step-wedge phantom that consists of sections ranging from 0 to 100% glandular, in 25% increments. The photons are then recorded on an ideal, energy-integrating detector in the absence of scatter or glare. A section of the phantom is replaced with breast material that has been mixed with a certain concentration of silver. In this manner, simulated high- and low-energy images were acquired and then subtracted using the weighting factors calculated in (8).

Spectral Optimization

A spectral simulation search was performed to identify the combination of clinically-feasible imaging parameters that maximized contrast for Ag. The parameters chosen for the search are limited to those that are experimentally feasible on the Hologic CEDE Dimensions system.

TABLE 3

| Parameters used for the spectral search. | |
| --- | --- |
| Parameter | Values |
| Target | Tungsten |
| Low Energy kVp | 23 to 32 |
| High Energy kVp | 36 to 49 |
| Filter Materials | Low Energy: Ag, Rh, Al |
| | High Energy: Cu |
| | All spectra were pre-filtered with 50 |
| | cm of air and 0.7 mm Be |
| Detector | SL energy-integrating |

Polyenergetic tungsten spectra were simulated using Boone's interpolation method and filtered using the Beer-Lambert law. The signal intensity recorded on the detector was calculated as:

$$SI = \sum_{E=1}^{kVp} N_E \times F_m \times F_d \times E \qquad (10)$$

where:

$N_E$ is the number of photons at the energy E, calculated using Boone's method (Boone J M, Fewell T R, Jennings R. *Molybdenum, rhodium, and tungsten anode spectral models using interpolating polynomials with application to mammography*. Med Phys. 1997 December; 24(12): 18634874).

$F_m = e^{\Sigma(-\mu t)}$ for all materials present in the beam path $F_d = (1 - e^{-(\mu t)_d})$ for the detector (d)

The standard deviation, $\sigma$, of the signal intensity was calculated as:

$$\sigma = SI^{0.46} \qquad (11)$$

The coefficient of 0.46 was obtained from Marshall et al. where the noise in a Hologic Selenia system was characterized. A low- and high-energy spectral pair were then passed through either a block of 100% adipose or 100% glandular tissue. W can be calculated using signal intensities (SI) as:

$$W = \frac{\ln\left(SI_a^H\right) - \ln\left(SI_g^H\right)}{\ln\left(SI_a^L\right) - \ln\left(SI_g^L\right)} \qquad (12)$$

Equation 12 can be thought of as the equivalent of Equation 8 for a polyenergetic spectra. The spectral pair used for the calculation of W was then instead passed through a block with a 15 50% glandular fraction. $SI^{DE}$ was calculated in the presence $$\left(SI_{Ag}^{DE}\right)$$

and absence $$\left(SI_{bkg}^{DE}\right)$$

of a silver contrast agent at a concentration of 1 mg/cm². The signal difference to noise ratio (SDNR) was chosen as the figure of merit to be maximized in the optimization, and was calculated as:

$$SDNR = \frac{SI_{Ag}^{DE} - SI_{bkg}^{DE}}{\sigma_{bkg}^{DE}} \qquad (13)$$

where:

$$\sigma^{DE} = \sqrt{\sigma^{2^H} + W^2 \times \sigma^{2^L} - 2 \times W \times \text{cov}\left(\ln\left(SI_{bkg}^H\right), \ln\left(SI_{bkg}^L\right)\right)} \qquad (14)$$

The covariance term was assumed to be a constant and determined experimentally by obtaining a DE image set of a plain sheet of acrylic, and then calculating the correlation between the signals in a fixed region of interest.

To ensure that the results would produce an optimization point that was clinically feasible, several constraints were applied to the simulation algorithm.

The total effective dose to the breast was set at 2.4 mGy. However, the manner in which this dose was distributed between the low- and high-energy spectra was allowed to vary. The mean glandular dose to the breast for a given spectrum was calculated using Hendee (Hendee W R, Ritenour E R. Medical Imaging Physics. 4$^{th}$ ed. Wiley-Liss (NY); 2002.) and Dance (Dance D R. *Monte Carlo calculation of conversion factors for the estimation of mean glandular breast dose*. Phys Med Biol. 1990; 35(9):1211-1219).

The mAs required to achieve the desired dose was not allowed to exceed 200 m As. The required mAs for a given dose was estimated using experimentally-obtained tube output data.

A minimum threshold detector signal intensity was set.

Spectral Optimization Validation

A 4 cm step phantom was imaged on the Hologic clinical CEDE Dimensions system. A silver foil, measuring 50 jam in thickness, was taped on top of the phantom to mimic an embedded concentration of 25 mg/cm² of Ag contrast agent. The phantom was imaged at the optimal conditions found in the previous section as well as other non-optimal combinations of parameters. The low- and high-energy images were then subtracted using the appropriate weighting factors to eliminate the glandular dependence. SDNR was then calculated for each of the DE images. The experimental and simulated values of W and SDNR were compared to validate the simulation algorithm.

Results

Imaging Framework

W (see FIG. 8) and $S_C$ of silver (see FIG. 9) were calculated for energy combinations between 20 and 50 keV. W was found to have values ranging between 0 and 1—this is to be expected as the difference in mass attenuation coefficients of adipose and glandular tissue decreases as the energy increases. tends towards 1 along the diagonal of the plot, for the case where the low and high energy are equal, and is smallest when the low- and high-energies are furthest apart.

As expected, $S_C$ is only significantly greater than zero for energy pairs that bracket the k-edge. The maximum contrast, however, does not occur directly above and below the k-edge but at (21,26) keV. This is due to the effect that the weighting factor, and consequently the attenuation coefficients of adipose and glandular tissue, have on $S_C$. Similarly, $S_C$ was calculated for iodine, and plotted in FIG. 10. The maximum achievable contrast when using iodine is 33% lower than 10 that of silver.

Monoenergetic Simulations

FIG. 11 shows the simulated low- and high-energy images that are obtained using an energy pair of (21, 26) keV. Each of the single energy images demonstrates a strong SI-dependence on the glandular fraction of the underlying tissue. The section of the phantom that contains Ag, consists of a singular concentration of the element, but results in a gradient of signal intensities because of the underlying variations in soft-tissue composition. By subtracting these single-energy images using W calculated for that energy pair, the DE image shown on the right was obtained.

Spectral Optimization and Validation

Five spectral pairs, including the optimization maximum, were chosen to validate the simulation results (see Table 4). FIG. 12 shows the experimentally-determined W plotted against the simulated values. The two sets of data are shown to be highly correlated, with the experimental values assuming a scalar multiple of the simulated data. This scalar is due to the manner in which the Hologic CEDE converts the total number of x-ray photons into digital values.

The SDNR simulated for each of these spectra was compared to the experimentally-obtained values and plotted in FIG. 13. The two sets of data are found to be correlated with a coefficient of determination, $R^2$, of 0.9407. Spectral Pair 1 was identified as the optimization maximum in the simulation algorithm, and also showed the maximum experimental SDNR. An identical simulation algorithm was run for an iodine contrast agent, and the maximum SDNR was calculated to be 15% lower than that of Spectral Pair 1.

Low- and high-energy images, along with the DE subtraction, are shown in FIG. 14 for the step phantom imaged using Spectral Pair 1. A line segment (vertical line on the left side of the DE subtraction image), spanning all glandular fractions, was placed in each of the DE, low-, and high-energy images. The mean ($\gamma$) and standard deviation ($\sigma$) of the SI of the pixels in a given image were then calculated, and the coefficient of variation cv of the background SI was computed as:

$$c_v = \frac{\gamma}{\sigma} \tag{15}$$

Similarly, six regions of interest in (FIG. 14, shown as 5 squares over the silver and one circle over the background) were used to calculate the SDNR at five locations of the phantom marked with squares. $c_v$ of the SDNR and background SI are tabulated in Table 5. In each case, $c_v$ is smallest in the DE image.

TABLE 4

Spectra chosen for validation of optimization results. The table includes the high- and low- energy kVp and filter choice along with the dose fraction to the low-energy spectrum. The optimization maximum is highlighted in gray.

| Spectral Pair | High Energy | Low Energy | Dose fraction to LE |
|---|---|---|---|
| 1 | 46-Cu | 27-Rh | 0.5 |
| 2 | 49-Cu | 27-Al | 0.6 |
| 3 | 49-Cu | 54-Ag | 0.6 |
| 4 | 49-Cu | 33-Rh | 0.8 |
| 5 | 40-Cu | 35-Al | 0.8 |

TABLE 5

Coefficient of variation, $c_v$ for the background SI and SDNR in each of the DE, low- and high-energy images. For both cases, $c_v$, of the DE image is the smallest.

| $c_v$ | DE | Low-Energy | High Energy |
|---|---|---|---|
| Background SI | 0.072 | 0.71 | 0.12 |
| SDNR | 0.0036 | 0.28 | 0.0095 |

DISCUSSION AND CONCLUSIONS

In this Example, a DE subtraction method for silver that would remove soft tissue signal variation while preserving the contrast from the imaging agent was developed. A framework was developed in Equations 1 through 9 using a monoenergetic analysis of the signal intensities obtained from a low- and high-energy acquisition. The weighting factor, W, that is needed to be applied to the low-energy image in the DE subtraction is formulated in Equation 8. W is independent of the choice of contrast material, and solely depends on the low- and high-energy attenuation coefficients of adipose and glandular tissue. W is plotted in FIG. 8 for combinations of energies ranging from 20 to 50 keV. assumes values between 0 (when the low- and high-energies are furthest apart) and 1 (for the trivial case when the low- and high-energy are the 15 same).

The theoretical DE contrast, $S_C$, observed from an imaging agent is formulated in Equation 9. $S_C$ is plotted in FIGS. 9 and 10 for silver and iodine, respectively. For both materials, $S_C$ is only significantly greater than zero at energy pairs that bracket the k-edge of the material (25 keV—silver, 33 keV—iodine). Interestingly, the maximum value of $S_C$ does not occur directly above and below the k-edge where the difference between the attenuation coefficient is the greatest. Instead, Sc of silver is maximum at an energy pair of (LE,HE)=(21, 26) keV. This is due to the effect that the weighting factor, and consequently the attenuation coefficients of adipose and glandular tissue, have on $S_C$. The maximum achievable contrast of iodine is 33% lower than that of silver, implying that a silver contrast agent is better suited as a DE imaging agent in the mammographic energy range.

A monoenergetic image acquisition was then simulated using the energy pair (21,26) keV that maximized Sc of silver. FIG. 11 shows the DE, low-, and high-energy images that were obtained. The DE image demonstrates two important features for CEDE imaging. First, the soft-tissue contrast has been nullified. The background signal has been reduced to a single value that is independent of the glandular percentage. Second, the contrast in the silver is maintained and independent of the underlying soft-tissue composition.

A polyenergetic simulation was then performed to identify the set of clinically-feasible imaging parameters that optimized the contrast for silver. In this particular study, the optimization was performed for a Hologic CE-DBT system; parameters listed in Table 3. The simulation was further constrained to ensure that the total mean glandular dose to the breast was 2.4 mGy. The optimal imaging technique consisted of a 46 kVp high-energy beam and a 27 kVp low-energy beam with rhodium filtration, at a dose distribution of 50:50. This low-energy technique is a classic example of an anatomical image that is obtained in the clinic today. In the case of an iodine agent, this low-energy kVp would need to be higher to accommodate for the higher k-edge of iodine. Further supporting that silver is a superior DE imaging agent to iodine in the mammographic energy range.

Table 4 shows the four additional spectral pairs that were chosen to test the validity of the simulation algorithm identifying Spectral Pair 1 as the optimization point. The experimental values of W for each of the spectral pairs was shown to correlate well with the simulated numbers as shown in FIG. 12. The inability to perfectly estimate W arises from the inability to exactly simulate the conversion of x-ray photons absorbed in the detector to digital units. As shown in FIG. 13, the experimentally-determined SDNR was shown to highly correlated with the simulated values. Spectral Pair 1 proved to maximize the SDNR in both the experiments and simulations. Additionally, the maximum simulated SDNR for an iodine agent is 15% lower than that of Spectral Pair 1, further supporting that silver is a better DE imaging agent in the mammographic energy range.

DE, low-, and high-energy images of the step phantom imaged using Spectral Pair 1 is shown in FIG. 14. The coefficient of variation, $c_v$, of the background SI and the SDNR of the silver at various locations in the phantom are tabulated in Table 5. In both cases, the DE image demonstrates the lowest $c_v$. This indicates that the DE subtraction succeeded in removing the soft-tissue signal variation present at the single-energy images, as well as maintaining the SDNR of a silver contrast agent regardless of the underlying soft-tissue composition. By applying the DE subtraction described here, a silver-based agent will outperform an iodinated contrast agent on a commercially-available CEDE breast x-ray imaging system.

Example 3

This Example presents a method to produce encapsulated silver nanoparticles for medical imaging, so as to reduce the toxicity of the silver. The encapsulated silver nanoparticles have a silver core, which is encapsulated by a silica shell, which is then encapsulated and a PEG coating. The silver provides radiographic contrast, the silica reduces the toxicity from the silver, and the PEG improves the biocompatibility of the nanoparticle. The toxicity of silver nanoparticles is believed to arise from the oxidation of the surface of the particles and consequent release of silver ions ($Ag^+$) into the surrounding environment. Encapsulation of the silver core with a silica shell will reduce the formation and release of these silver ions.

Step 1: Production of Silver Core

The silver core was fabricated using the method of Silvert el al. ("Preparation of colloidal silver dispersions by the polyol process. Part 1—Synthesis and characterization" *J Matter Chem*, 6(4): 573-577, 1996). This method was chosen as it allowed for the synthesis of polyvinylpyrrolidone coated silver nanoparticles that can directly be used in the silica-encapsulation step.

Briefly, 1.5 g of polyvinylpyrrolidone (PVP, molecular weight: 10,000 Da) was dissolved in 75 mL of ethylene glycol in a 250 mL round bottom flask equipped with a magnetic stirrer. This mixture was allowed to stir for 12 hours in the dark. 50 mg of silver nitrate was then added to the solution, which was then allowed to stir for 1 hour or until complete dissolution of the silver nitrate. The reaction flask was then heated to 120° C. at a constant rate of 1° C./min. The reaction was allowed to proceed at this temperature for 1 hour. Once the reaction had been completed, the silver nanoparticle solution was cooled in a water bath at room temperature. The particles were separated from the ethylene glycol by addition of 500 mL of acetone, followed by centrifugation at 4000×g for 15 minutes. The filtrate was removed and the particles were resuspended in ethanol for the silica encapsulation step.

FIG. 15 shows a transmission electron micrograph of the synthesized PYP-coated silver nanoparticles. The average diameter of the particles was measured to be 39±6 nm (mean±standard deviation).

Step 2: Coating the Silver Core to Produce the Silica-Silver Nanoparticle

The silver nanoparticles were encapsulated with a silica shell using the method of Graf et al. ("A general method to coal colloidal particles with silica" *Langmuir.* 19:6693-6700, 2003.). The silver nanoparticles were purified through centrifugation cycles at 20,000×g for 15 minutes. The particles were finally resuspended in 9.484 mL of ethanol in a 25 mL round bottom flask, 415 µL of ammonium hydroxide was added to the nanoparticle solution, immediately after which 75 µL of tetraethoxysilane (TES) (in 675 µL of ethanol) was added. The reaction was allowed to proceed for 12 hours under vigorous stirring.

Figure 16:
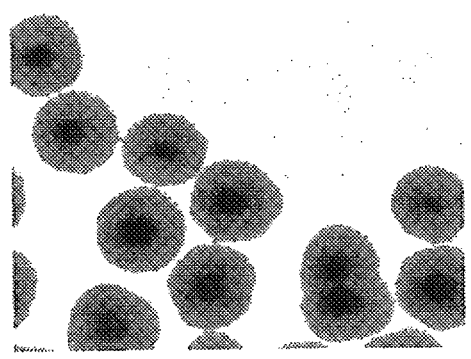

FIG. 16 shows a transmission electron micrograph of the silica-silver nanoparticles. The average diameter of the particles was measured to be 102±9 nm, including the silver core and silica shell.

Step 3: Coating the Silica-Silver Nanoparticle to Produce a PEG-PCL-Coated Nanoparticle The silica-silver nanoparticles were coated with polyethylene glycol using a modified method of Koole et al. ("Paramagnetic lipid-coated silica nanoparticles with a fluorescent quantum dot core: A new contrast agent platform for multimodality imaging" *Bioconjugate Chemistry,* 19: 2471-2479, 2008.). Briefly, the silica-silver nanoparticles were purified again using centrifuge cycles at 18,000×g for 15 minutes, and resuspended in 5 mL of ethanol. 1.5 g of octadecanol, dissolved in 5 mL of ethanol, was then added to the nanoparticle solution in a 50 mL round bottom flask. The flask was then fitted with a distillation apparatus and heated to 100° C. for 1 hour to remove the ethanol. The temperature was then raised to 170° C. for 3 hours to covalently link the octadecanol to the silica shell by a condensation reaction. The octadecanol-coated silica-silver nanoparticles were then resuspended in toluene, and purified by centrifugation at 18,000×g for 15 minutes. The particles were then resuspended at a final concentration of 40 mg/mL. 100 μL of this solution was then added to 4 mg of polyethylene glycol (PEG, 4000 Da)-polycaprolactone (PCL, 3000 Da) diblock polymer in 100 μL of toluene. The mixture was then added to 4 mL of de-ionized water under sonication. The toluene was allowed to evaporate, and the (PEG-PCL)-coated silica-silver nanoparticles were purified through a combination of centrifugation and syringe filters.

Example 4

PEG-Stabilization of Silica-Silver Nanoparticles

The silver core and silica shell were synthesized using the method described in Example 3. In Example 4, the silica-encapsulated nanoparticles were functionalized with terminal amine groups to attach the PEG ligands. The nanoparticles were reacted with 3-aminopropyl-trimethoxysilane under gentle stirring for 12 hours at room temperature, after which the temperature of the reaction was brought up to 55° C. for 1 hour. The amine-terminated silica silver nanoparticles were resuspended in phosphate buffered saline (PBS) following purification. The particles were then mixed with a mass excess of PEG-N-hydroxysuccinimide (NHS) and allowed to react for 2 hours under vigorous stirring at room temperature. The PEG-coated silica-silver nanoparticles (PEG-SiAg) were then purified using a combination of centrifugal and 0.2 μm surfactant-free cellulose acetate (SFCA) syringe filters to remove any unwanted byproducts and excess reagents.

The physical diameter of the nanoparticles at various stages of the synthesis was measured using transmission electron microscopy (TEM). The PVP-coated silver cores are shown in FIG. 15. The particles consisted of solid, spherical silver cores with an average diameter of 39±6 nm (mean±standard deviation). After silica encapsulation, the total diameter of the nanoparticles was 102±9 nm (FIG. 16). The majority of the silica-silver nanoparticles consisted of a single silver core covered by a spherical silica shell. The PEG layer of the final PEG-SiAg was electron-transparent and thus did not appear in the TEM micrograph (FIG. 17). The particles were however, observed to be separated from each other indicating that a polymeric surface layer was successfully attached to each silica-silver nanoparticle. The hydrodynamic diameter and zeta potential of PEG-SiAg was determined to be 115.3 nm and 0.065 mV, respectively. The difference of 13.2 nm between the physical and hydrodynamic diameters help support the assertion that the PEG ligands were successfully attached to the Si surface.

DE Imaging of Mice Using PEG-SiAg—Intravenous Injection

PEG-SiAg nanoparticles formed by the process above were injected via the tail vein, into immunocompromised female mice. The mice were maintained under anesthesia for the entirety of the imaging procedure using inhaled isoflurane. The animals were imaged using a GE Senographe DS mammography unit. The HE and LE spectra were selected as 49 kV rhodium beam with rhodium filtration and a 26 kV molybdenum beam with molybdenum filtration, respectively. The LE kV was set just below the k-edge of Ag, while the HE kV was set to the maximum possible on the imaging system to minimize overlap between the two spectra. Regions of interest were chosen in the soft tissue (s) and bone (b) in the LE or HE images. The weighting factor, W, was calculated using the average signal intensities (SI) of the two regions:

$$W = \frac{\ln\left(SI_b^{HE}\right) - \ln\left(SI_s^{HE}\right)}{\ln\left(SI_b^{LE}\right) - \ln\left(SI_s^{LE}\right)}.$$

The DE image was calculated as the weighted logarithmic subtraction between the LE and HE image.

$$DE = \ln(HE) - W \times \ln(LE)$$

Prior to the subtraction, the HE image was registered to the LE image using the Image Processing Toolbox in MATLAB (MathWorks, Natick, MA).

The LE, HE, and DE images of the animal prior to the injection of the PEG-SiAg are shown in FIG. 18. The single-energy images (LE and HE) show good contrast between the various tissue types, allowing for straightforward discrimination between bone and soft tissue. The anatomical contrast (i.e., bone and soft tissue) was, by and large, removed in the DE image.

The corresponding images obtained after the injection of PEG-SiAg are shown in FIG. 19. As in the pre-contrast images, the anatomical signal variation had been suppressed in the DE image compared to the single-energy images (LE, HE). However, the signal arising from the silver contrast agent (indicated with arrow) had been preserved, thereby increasing its conspicuity. The SDNR was calculated as 11.6, 17.1, and 26.2 in the LE, HE, and DE images respectively, indicating a 53 to 126% improvement in the contrast of the silver in the DE image compared to the single-energy images. The particles showed no toxic effects, acutely or otherwise, and the animal was still alive 2.5 weeks post-injection.

Blood Clearance/Biodistribution

PEG-SiAg were injected intravenously into three immunocompromised female mice. 10 μL samples of blood were obtained at various time points pre- and post-injection (5 mins, 10 mins, 15 mins, 30 mins, 1 hour, 2 hours, 4 hours, 8 hours, 24 hours). The animals were sacrificed 24 hours after the injection of the particles. The organs of the animals were harvested and digested, along with the blood samples, using 1 M nitric acid at room temperature for 12 hours. The blood and organ samples were diluted with de-ionized water to a total volume of 6.0 mL. The silver content was then measured using inductively-coupled plasma optical emission spectroscopy (ICP-OES).

The blood clearance and biodistribution results are shown in FIG. 20 and FIG. 21, respectively. The particles are rapidly removed from the bloodstream with an estimated half-life of 13-17 minutes, and taken up by the liver and spleen. Significant accumulations of silver were also detected in the lymph node, pancreas, large bowel and muscle.

DE Imaging of Mice Using PEG-SiAg—Intraperitoneal Injection

PEG-SiAg nanoparticles formed by the process above were intropeitoneally injected into immunocompromised female mice. Examples of the LE, HE, and DE images of the animal after the intraperitoneal injection of the PEG-SiAg are shown in FIG. 22. The suppression of the anatomical signal variation in the DE image allowed for clear identification and segmentation of the peritoneal organs after the surrounding space has been filled with the silver contrast material. The progression of the contrast in the peritoneal cavity over time is illustrated in FIG. 23. Images were taken after (a) 5 minutes, (b) 20 minutes, (c) 40 minutes, and (d) 50 minutes post-injection. The outline of the peritoneal organs decreased steadily over time, as the contrast agent was taken up into the bloodstream. Little contrast was observed in the peritoneum 50 minutes after the injection of the nanoparticles.

DE Imaging of Mice Using PEG-Si/Ag—Subcutaneous Injection

PEG-SiAg nanoparticles formed by the process above were subcutaneously injected into immunocompromised female mice. Examples of the LE, HE, and DE images of the animal after the subcutaneous injection of the PEG-SiAg are shown in FIG. 24. The site of injection is indicated by the arrow in FIG. 24(c). The bolus of contrast material can be identified in all three images. However, the DE image was able to discriminate between the injected nanoparticles and the underlying anatomic bone structures. The boundaries of the bolus injection was also easily identified and separated from the surrounding tissue structures.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A contrast agent for x-ray imaging comprising stabilized metal nanoparticles, wherein a stabilized metal nanoparticle comprises a metallic core selected from the group consisting of a silver nanoparticle, a rhodium nanoparticle, a palladium nanoparticle, a cadmium nanoparticle, a bismuth nanoparticle, a zirconium nanoparticle, a tin nanoparticle, a gold nanoparticle, a platinum nanoparticle, and a molybdenum nanoparticle, and wherein a stabilized metal nanoparticle further comprises a shell and a coating disposed on the shell, wherein (1a) the shell comprises silica, or (1b) the shell comprises (i) a hydrophobic polymer, (ii) an oil, or both (i) and (ii), or (2) the coating comprises polyvinylpyrrolidone (PVP), PEG-polycaprolactone (PCL), PEG-polylactic acid (PLA), PEG-poly(lactic-co-glycolic acid (PLGA), polyvinyl alcohol (PVA), amine-modified or unmodified poly(maleic anhydride-alt-1-octadecene) (PMAL), PEG-phospholipids, or phospholipids, or (3) both (1a) and (2), or (4) both (1b) and (2).

2. The contrast agent according to claim 1, wherein said stabilization avoids cytotoxicity.

3. The contrast agent according to claim 1, wherein said stabilization avoids immunoreactivity.

4. The contrast agent according to claim 1, wherein said contrast agent lacks an active targeting agent.

5. The contrast agent according to claim 1, wherein said contrast agent comprises a targeting ligand that targets said contrast agent to one or more types of tumors.

6. The contrast agent according to claim 5, wherein said one or more types of tumors are breast tumors.

7. The contrast agent according to claim 5, wherein said targeting ligand is selected from the group consisting of an antibody, antibody fragment, protein, peptide, small molecule, or an aptamer.

8. The contrast agent according to claim 1, wherein the metallic core is a silver nanoparticle and wherein the metallic core is synthesized using the Brust method in water or the Silvert method.

9. The contrast agent according to claim 1, wherein said stabilized metal nanoparticles are stabilized with polyethylene glycol (PEG).

10. The contrast agent according to claim 9, wherein said PEG has a molecular weight ($M_w$) of about 5000.

11. The contrast agent according to claim 9, wherein said metallic core is a silver nanoparticle and wherein and a molar ratio between the PEG and the silver is about 1.5:1.

12. The contrast agent of claim 1, wherein said metallic core is a silver nanoparticle.

13. The contrast agent of claim 1, wherein said metallic core is a rhodium nanoparticle, a palladium nanoparticle, a cadmium nanoparticle, a bismuth nanoparticle, a zirconium nanoparticle, a tin nanoparticle, a gold nanoparticle, a platinum nanoparticle, or a molybdenum nanoparticle.

14. The contrast agent of claim 12, wherein said a coating comprises polyvinylpyrrolidone (PVP).

15. The contrast agent of claim 1, wherein said shell comprises silica.

16. The contrast agent of claim 1, wherein said coating comprises PEG-polycaprolactone (PCL), PEG-polylactic acid (PLA), PEG-poly(lactic-co-glycolic acid (PLGA), polyvinyl alcohol (PVA), amine-modified or unmodified poly(maleic anhydride-alt-1-octadecene) (PMAL), PEG-phospholipids, or phospholipids.

17. The contrast agent of claim 1, wherein said metallic core has an average diameter from about 0.5 mm to about 100 nm.

18. The contrast agent of claim 1, wherein said shell has an average thickness from about 10 nm to about 150 nm.

19. The contrast agent of claim 1, wherein a stabilized nanoparticle has an average diameter from about 15 nm to about 200 nm.

20. The contrast agent of claim 1, wherein the shell comprises (i) a hydrophobic polymer, (ii) an oil, or both (i) and (ii).

21. The contrast agent of claim 20, wherein the hydrophobic polymer comprises at least one of poly(lactic-co-glycolic acid (PLGA) or polylactic acid (PLA).

22. The contrast agent of claim 1, wherein the stabilized metal nanoparticles are individual metal nanoparticles.

23. The contrast agent of claim 1, wherein (1b) the shell comprises (i) a hydrophobic polymer, (ii) an oil, or both (i) and (ii), or (2) the coating comprises polyvinylpyrrolidone (PVP), PEG-polycaprolactone (PCL), PEG-polylactic acid (PLA), PEG-poly(lactic-co-glycolic acid (PLGA), polyvinyl alcohol (PVA), amine-modified or unmodified poly(maleic anhydride-alt-1-octadecene) (PMAL), or PEG-phospholipids, or phospholipids, or (4) both (1b) and (2).

* * * * *